United States Patent [19]
Blacklock et al.

[11] Patent Number: 5,733,123
[45] Date of Patent: Mar. 31, 1998

[54] HEALING CAP FOR IMPLANT ANCHOR

[76] Inventors: Gordon D. Blacklock, 3321 Columbia NE., Albuquerque, N. Mex. 87107; Americo Fernandes, #3 Carmarthen Blvd., Winnipeg, Manitoba, Canada, 43POW3

[21] Appl. No.: 606,004

[22] Filed: Feb. 12, 1996

[51] Int. Cl.$^6$ ............................................. A61C 8/00
[52] U.S. Cl. ................................. 433/173; 433/172
[58] Field of Search ........................... 433/172, 173, 433/174, 175, 176

[56] References Cited

U.S. PATENT DOCUMENTS

| | | | |
|---|---|---|---|
| 4,856,994 | 8/1989 | Lazzara et al. | 433/173 |
| 5,030,096 | 7/1991 | Hurson et al. | |
| 5,154,612 | 10/1990 | Carlsson et al. | |
| 5,195,891 | 3/1993 | Sulc | 43/173 |
| 5,213,500 | 5/1993 | Salazar et al. | 433/173 |
| 5,417,569 | 5/1995 | Perisse | 433/173 |
| 5,417,570 | 5/1995 | Zuest et al. | |
| 5,437,551 | 8/1995 | Chalifoux | |
| 5,468,150 | 11/1995 | Brammann | 433/173 |

FOREIGN PATENT DOCUMENTS

| | | | |
|---|---|---|---|
| 3300764 | 7/1984 | Germany | 433/173 |
| 1169644 | 7/1985 | Russian Federation | 433/172 |
| 93020773 | 10/1993 | WIPO | 433/173 |

*Primary Examiner*—Ralph Lewis
*Attorney, Agent, or Firm*—Terrance Siemens

[57] ABSTRACT

A healing cap for an anchor of a dental implant anchor. The healing cap has a cylindrical head having an opening at the top side, and two legs projecting downwardly from the head. The opening at the top side has threads for receiving a threaded tool which will subsequently be employed to withdraw the healing cap from the anchor. The legs are separated by a gap enabling the legs to be urged toward one another when the healing cap is inserted into the anchor. The legs are of lesser diameter than that of the cylindrical head, so that the head can seal the opening of the anchor when the healing cap is fully inserted into the anchor. The legs resiliently resist compression from being forced into the opening of the anchor. This arrangement causes frictional engagement with the anchor which secures the healing cap to the anchor. The novel healing cap enables an anchor to be employed which lacks threads for engaging the healing cap, thereby reducing cost of fabricating the anchor.

5 Claims, 2 Drawing Sheets

HEALING CAP FOR IMPLANT ANCHOR

BACKGROUND OF THE INVENTION

1. Field of the Invention

The present invention relates to a healing cap for an anchor for a dental implant. The anchor is implanted in bone tissue of a patient. The healing cap protects the upwardly oriented opening of the anchor, which will subsequently receive a post and core assembly, from being obstructed by regenerated gum tissue and other possible contaminants.

2. Description of the Prior Art

When an anchor for receiving a post and core assembly of a dental prosthesis is initially installed in a patient's jaw, care must be exercised to assure that the opening not become clogged due to regenerated gum tissue or other materials. A temporary sealing member, called a healing cap or cuff, is ordinarily provided for sealing the anchor while bone tissue grows around and solidifies the anchor in the jaw. Most healing caps thread into the anchor, which has a hexagonal opening for receiving the post and core. After removal of the healing cap, the threads play no role.

Forming threads within the opening of the anchor, particularly when this opening is generally hexagonal, increases complexity and hence cost of the anchor. It would be desirable to avoid providing threads within this opening.

A healing cap is seen in U.S. Pat. No. 5,030,096, issued to Steven M. Hurson et al. on Jul. 9, 1991. This healing cap has an upwardly oriented opening for resiliently receiving a grasping member which can be withdrawn from the cap after installation of the latter in the anchor. However, the opening is plain, lacking threading or other structure for interfitting engagement of a tool or key for removing the cap when it is time for removal thereof from the anchor. By contrast, the present invention has structure which enables a key or like tool to engage the cap for positive retention during removal. However, the cap of Hurson et al. has threads for engaging the opening of the anchor. Such threads are absent in the present invention.

U.S. Pat. Nos. 5,154,612, issued to Lennart Carlsson et al. on Oct. 13, 1992, and 5,417,570, issued to Max Zuest et al. on May 23, 1995, both feature caps which lack threads for engaging an anchor. However, in both prior art examples, the cap externally surrounds the anchor or other part of the implant engaged by the cap. In contrast to this, the novel healing cap penetrates and engages the same opening which will subsequently be employed to receive the post and core of the prosthesis.

A member which penetrates an anchor and engages the same by friction is shown in U.S. Pat. No. 5,437,551, issued to Paul R. Chalifoux on Aug. 1, 1995. However, the top of this member is plain, lacking an opening and associated structure for interfittingly engaging a key or other tool which may be employed to withdraw the member. In contrast to the device of Chalifoux, such an opening and associated structure are found in the present invention.

None of the above inventions and patents, taken either singly or in combination, is seen to describe the instant invention as claimed.

SUMMARY OF THE INVENTION

The present invention allows the use of an anchor which lacks threading of the hexagonal opening conventionally employed to engage a healing cap. Instead, the healing cap employs resilient resistance to compression when being inserted into the opening of the anchor to create friction maintaining the cap in place.

While this arrangement may seem much less secure than conventional threaded engagement, the fact is that little force is actually required to secure the healing cap in the anchor. This is because while chewing imposes strong forces which urge the healing cap into the anchor, there are no corresponding forces acting to remove the healing cap from the anchor. Moreover, the cap is only temporarily installed, and will be subsequently removed when the anchor is firmly secured within the jaw.

The anchor is a permanent device, and hence must be fabricated with great precision in permanent materials. It is generally desirable to minimize complexity, and hence cost, of the anchor. One way to accomplish this is to eliminate threading conventionally employed only to secure the healing cap during its temporary placement in the anchor.

To this end, the novel healing cap has a cylindrical head from which depend opposed legs which resiliently compress when inserted into the opening of the anchor. Consequent resilient expansion creates friction which secures the healing cap in place while the anchor is setting in the jaw. A small outwardly projecting flange further increases friction.

A single leg may be employed in lieu of the two separated legs described above, if resilient fit with the opening of the anchor were sufficient.

An advantage of this arrangement is that the force required to unseat the healing cap from the anchor is minimal. Also, the motion of removing the healing cap is quite short and economical, compared to tedious unthreading of a conventional healing cap.

The cylindrical head of the healing cap has an opening at its upper or top end for receiving a tool which will be employed to extract the healing cap from the anchor. This opening will be threaded, if it is desired to employ a threaded key to remove the healing cap. Alternatively, grooves for engaging a key, dental pick, or other tool are inscribed on the wall of the opening in the healing cap.

The cylindrical head of the healing cap is of greater diameter than that of the legs, so that the legs can penetrate the opening of the anchor, while the cylindrical head seals the opening of the anchor upon abutting the anchor.

Accordingly, it is a principal object of the invention to provide a healing cap for a dental implant anchor which penetrates the opening of the anchor while not threading to the anchor.

It is another object of the invention to provide a leg or legs engaging the anchor by friction arising from resilient resistance to compression upon penetrating the opening of the anchor.

It is a further object of the invention to enhance frictional engagement of the opening of the anchor by providing a flange disposed upon the leg or legs of the healing cap.

Still another object of the invention is to enable engagement of the healing cap by a tool which extracts the healing cap from the anchor by urging the healing cap upwardly, and not by turning or unthreading the healing cap.

An additional object of the invention is to seal the opening of the anchor upon abutment of the head of the healing cap with the anchor.

It is again an object of the invention to minimize the motions and effort of extracting the healing cap from the anchor.

It is an object of the invention to provide improved elements and arrangements thereof in an apparatus for the purposes described which is inexpensive, dependable and fully effective in accomplishing its intended purposes.

3

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein.

DETAILED DESCRIPTION OF THE PREFERRED EMBODIMENTS

Figure 1:
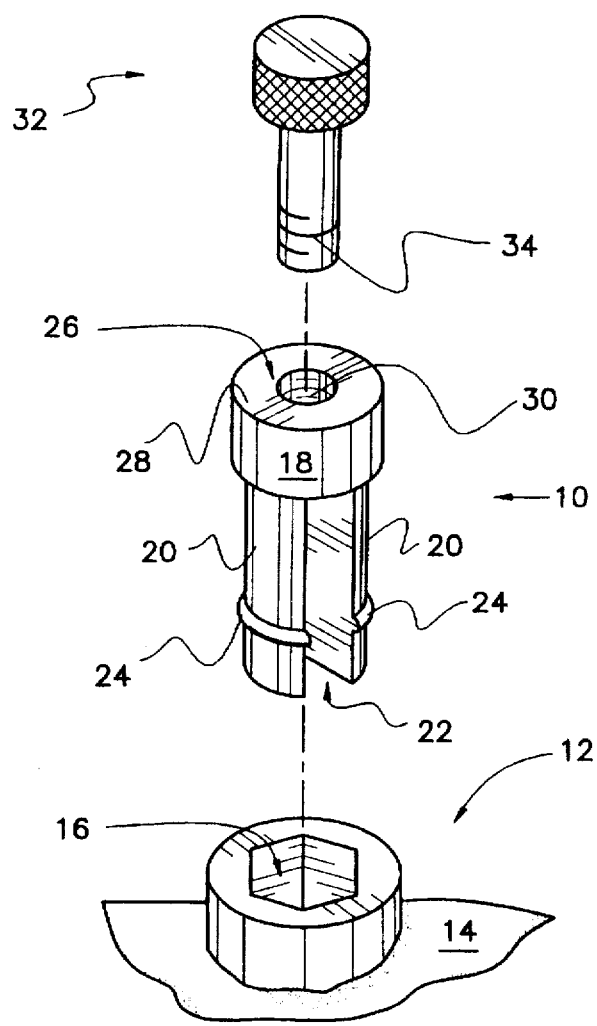
FIG. 1 is an environmental, perspective, exploded view of one embodiment of the invention wherein a threaded tool is employed to extract the healing cap from the anchor.

Turning now to FIG. 1 of the drawings, the novel healing cap 10 is shown above an anchor 12 implanted within bone tissue 14 of a patient's jaw (not separately shown). Anchor 12 has a conventional hexagonal opening 16 for receiving a post and core assembly (not shown) after securement of anchor 12 within the jaw as a result of tissue growth.

Healing cap 10 comprises a cylindrical head 18 from which depends a leg comprising two leg sections 20. Leg sections 20 are preferably complementary, separated by a slot 22 disposed therebetween, so as to collectively form a cylinder or any configuration which would cooperate with opening 16 of anchor 12. In this sense, cooperation signifies that when inserted into opening 16, leg sections 20 come to contact the wall of opening 16 in a generally symmetrical fashion, making contact at many points.

Healing cap 10 is preferably designed so that leg sections 20 are subjected to inward radial compression when inserted into opening 16. When plural leg sections 20 are provided, they will be urged towards one another during insertion. Slot 22 accommodates the slight consequent displacement of leg sections 20 as leg sections 20 approach one another during compression. Resilience of the material forming leg sections 20 causes force to be exerted against the lateral wall of opening 16 of anchor 12. This intimate contact causes friction maintaining healing cap 10 to remain within anchor 12.

The result of this cooperation is that healing cap 10 will be upright within and axially aligned with respect to anchor 12. Sufficient contact between leg sections 20 and the walls of opening 16 will exist as to cause enough friction to oppose ready withdrawal of healing cap 10 from anchor 12.

Healing cap 10 is formed from any suitable material which is biocompatible, durable, and which possesses requisite resilience. Metals which are chemically stable within the environment of the mouth, such as titanium, and a variety of synthetic polymers are examples of such materials.

4

It will further be seen in this Figure that head 18 is of greater diameter than that of leg sections 20. In this embodiment, leg sections 20 are plural in number, and have a collective or effective diameter encompassing both leg sections 20. The collective diameter of leg sections 20 corresponds to and is slightly greater than the diameter of opening 16 of anchor 12, for assuring frictional between leg sections 20 and anchor 12.

It would be feasible to provide any number of slots in order to form more than two leg sections 20, if desired, since such an arrangement will allow all leg sections to be displaced to the center.

In a further step to augment frictional engagement of the wall of opening 16 by leg sections 20, a short flange 24 projects externally from the periphery of each leg section 20. Flange 24 exerts inwardly directed, radially compressive force against its respective leg section 20, thereby causing resilience of leg sections 20 to further frictionally engage opening 16 of anchor 12.

The greater diameter of head 18 assures that head 18 will abut the top of anchor 12, thereby sealing opening 16 when healing cap 10 is fully inserted into opening 16.

Healing cap 10 is withdrawn from anchor 12 after healing by the following arrangement. An opening 26 is formed in the top end 28 of cylindrical head 18, and female threads 30 are disposed upon the lateral wall of opening 26. A key or tool 32 having male threads 34 corresponding to threads 30 turns into engagement with healing cap 10, and withdraws healing cap 10 by a short upward pull.

Figure 2:
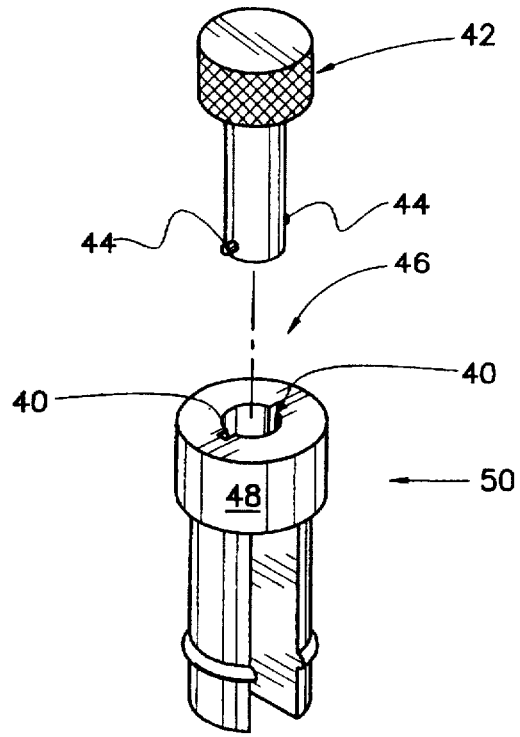
FIG. 2 is an environmental, perspective detail view of a second embodiment of the invention, wherein a key having projections is employed to remove the healing cap.

FIG. 2 shows an alternative embodiment of the invention wherein threads 30 of the first embodiment are replaced by L-shaped grooves 40. In this embodiment, key or tool 42 has projections 44 which interfittingly cooperate with grooves 40. Tool 42 is inserted downwardly into opening 46 of cylindrical head 48, then rotated slightly. Tool 42 can then be pulled upwardly to withdraw healing cap 50 from the anchor (see FIG. 1).

Figure 3:
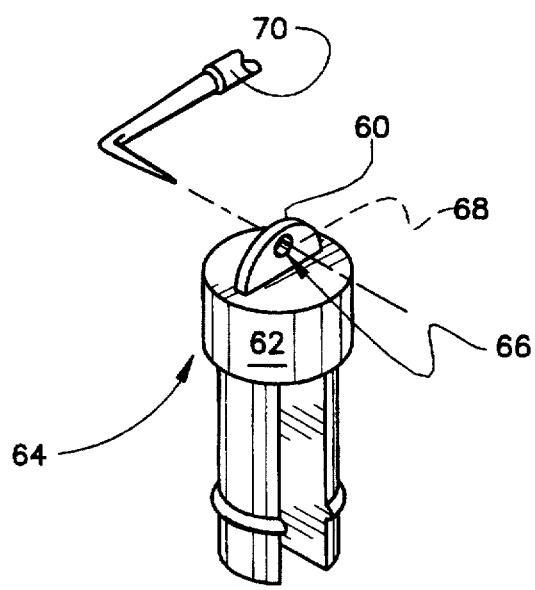
FIG. 3 is an environmental, perspective detail view of a third embodiment of the invention, wherein a dental pick is employed to remove the healing cap.

FIG. 3 shows a further alternative embodiment of the invention. In lieu of opening 30 or 46 of the previous embodiments, a projection 60 is disposed upon cylindrical head 62 of healing cap 64. Projection 60 has a hole 66 formed therein. Hole 66 has a downwardly oriented surface 68. A tool in the form of a dental pick 70 is inserted into hole 66, and lifts healing cap 64 by pulling upwardly against surface 68.

Figure 4:
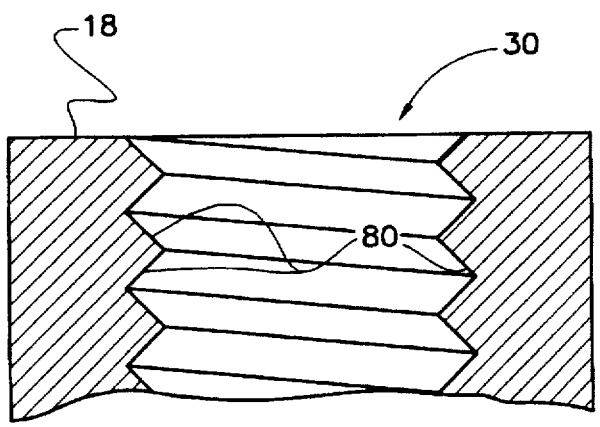
FIG. 4 is enlarged, cross sectional detail view of the embodiment of FIG. 1, and is taken from the center component of FIG. 1.

Each of the embodiments described above has a downwardly oriented surface corresponding to surface 68 of FIG. 3. In FIG. 4, threads 30 of the first embodiment are seen to include a helically arranged downwardly oriented surface 80, which surface 80 is engaged by corresponding male threads 34 (see FIG. 1) of tool 32.

Figure 5:
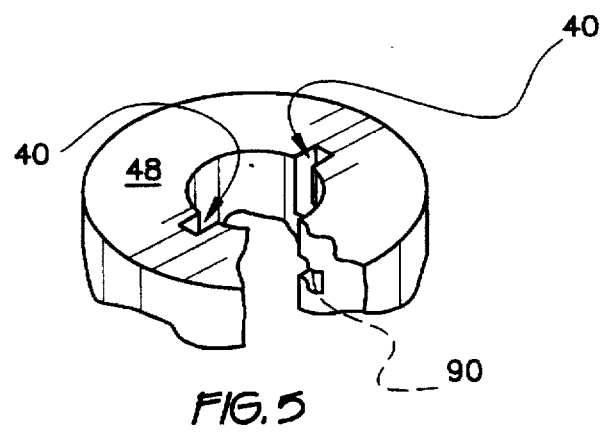
FIG. 5 is an enlarged, perspective detail view of the embodiment of FIG. 2, and is partially broken away to reveal internal detail.

Similarly, FIG. 5 shows a downwardly oriented surface 90 provided by each groove 40 of tool 42 (see FIG. 2). The respective members (head 18 of FIG. 1, head 48 of FIG. 2, or projection 60 of FIG. 3) each having one form of these downwardly oriented surfaces may be regarded as engagement members for enabling withdrawal or removal of healing cap 10 from an anchor. Each respective engagement member has a vertical surface or wall which is intersected by the respective downwardly oriented surface (provided by threads 30 in the embodiment of FIG. 1, shown in detail as surface 80 in FIG. 4, groove 40 of the embodiment of FIG. 2, shown in detail as surface 90 in FIG. 5, and surface 68 of hole 66 formed in projection 60 in the embodiment of FIG. 3.). It will be seen, then, that healing caps 10, 50, and 64 of the various embodiments are removed from the anchor by essentially similar operations.

It will occur to those of skill in the art that the invention is susceptible to various modifications and variations. For example, leg sections 20 could be superseded by a single leg. This will be acceptable provided the superseding arrangement has resilient or elastic resistance to compression upon insertion into the anchor, or other means for enhancing engagement with its anchor. Also, still other arrangements for engaging the healing cap for removal from the anchor may be devised.

It is to be understood that the present invention is not limited to the embodiments described above, but encompasses any and all embodiments within the scope of the following claims.

We claim:

1. A healing cap for closing the opening of an anchor of a dental implant, comprising:

a head having a diameter dimension and a top end, said head having an engagement member formed as part of said head, said engagement member cavity having vertical walls and a downwardly oriented surface formed in said vertical walls, said engagement member enabling a tool to engage said head for purposes of withdrawing said healing cap from the anchor by engaging said downwardly oriented surface by interference therewith and being pulled upwardly to remove said healing cap from the anchor; and a leg having means for providing resilient resistance to inward radial compression, said leg projecting downwardly from said head of said healing cap, said leg having a second diameter dimension along its entire length of magnitude less than that of said diameter dimension of said head of said healing cap, said leg having also having an externally projecting member formed thereon, projecting beyond said second diameter dimension, for frictionally engaging the opening of the anchor.

2. A healing cap for closing the opening of an anchor of a dental implant, comprising:

a head having a diameter dimension and a top end, said head having an engagement member formed as part of said head, said engagement member projecting upwardly from said head, said engagement member having a vertical wall and a hole formed in said vertical wall, said engagement member enabling a tool to engage said head for purposes of withdrawing said healing cap from the anchor by engaging said hole of said engagement member and being pulled upwardly to remove said healing cap from the anchor; and a leg having means for providing resilient resistance to inward radial compression, said leg projecting downwardly from said head of said healing cap, said leg having a second diameter dimension of magnitude less than that of said diameter dimension of said head of said healing cap, said leg having also having an externally projecting flange; extending beyond said second diameter dimension, for frictionally engaging the opening of the anchor.

3. The healing cap according to claim 2, said leg comprising at least two complementary leg sections and a slot disposed between each two of said two complementary leg sections, whereby said two complementary leg sections are urged towards one another when being inserted into the opening of an anchor, and exert resilient force against the lateral wall of the opening of the anchor.

4. The healing cap according to claim 2, said engagement member comprising an opening formed at said top end of said head, said opening having a vertical wall, said downwardly oriented surface being formed in said vertical wall of said opening.

5. A healing cap for closing the opening of an anchor of a dental implant, comprising:

a head having a diameter dimension and a top end, said head having an opening formed at said top end of said head, said opening further including a vertical wall and a downwardly oriented surface formed in said vertical wall of said opening, said opening and said downwardly oriented surface enabling removal of said healing cap from an associated anchor by inserting an object into said opening into interfering engagement with said downwardly oriented opening and pulling upwardly on the object; and at least two complementary leg sections each having means for providing resilient resistance to inward radial compression, and a slot disposed between each two of said at least two complementary leg sections, said at least two complementary leg sections projecting downwardly from said head of said healing cap, said at least two complementary leg sections having a collective second diameter dimension of magnitude less than that of said diameter dimension of said head of said healing cap, said at least two complementary leg sections each further having an externally projecting flange disposed thereon and extending beyond said second diameter dimension, whereby said at least two complementary leg sections engage the opening of the anchor by friction.

* * * * *